US012629454B2

(12) United States Patent
    Anderson et al.

(10) Patent No.: US 12,629,454 B2
(45) Date of Patent: May 19, 2026

(54) SYSTEMS AND METHODS FOR MAGNET-INDUCED ASSEMBLY TISSUE GRAFTS

(71) Applicant: The General Hospital Corporation, Boston, MA (US)

(72) Inventors: Richard Rox Anderson, Boston, MA (US); Joshua Tam, Boston, MA (US); Christiane Fuchs, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1137 days.

(21) Appl. No.: 17/606,956

(22) PCT Filed: Apr. 30, 2020

(86) PCT No.: PCT/US2020/030707
§ 371 (c)(1),
(2) Date: Oct. 27, 2021

(87) PCT Pub. No.: WO2020/223480
PCT Pub. Date: Nov. 5, 2020

(65) Prior Publication Data
US 2022/0193309 A1     Jun. 23, 2022

Related U.S. Application Data

(60) Provisional application No. 62/840,728, filed on Apr. 30, 2019.

(51) Int. Cl.
*A61B 17/322*     (2006.01)
*A61L 27/34*     (2006.01)
(Continued)

(52) U.S. Cl.
CPC .......... *A61L 27/446* (2013.01); *A61B 17/322* (2013.01); *A61L 27/34* (2013.01);
(Continued)

(58) Field of Classification Search
CPC .. A61F 2/105; A61F 2210/009; A61B 17/322; A61B 10/025; H01F 41/0273; A61M 35/00; A61L 27/362; A61L 27/28
(Continued)

(56) References Cited

U.S. PATENT DOCUMENTS 2,887,454 A * 5/1959 Toulmin, Jr. ........ H01F 41/0273
                                                           335/297
4,418,691 A   12/1983 Yannas
                (Continued)

FOREIGN PATENT DOCUMENTS

CN     101745147 A * 6/2010
WO     2001067814 A2   9/2001
                (Continued)

OTHER PUBLICATIONS

Translation of CN 101745147 (Year: 2010).*
                (Continued)

*Primary Examiner* — Brian E Pellegrino
(74) *Attorney, Agent, or Firm* — QUARLES & BRADY LLP

(57)     ABSTRACT

Systems and methods for assembling a plurality of tissue grafts are provided. A method includes applying a magnetic coating over a surface of a donor site and harvesting the plurality of micro tissue grafts from the donor site, so that an upper surface of each of the plurality of micro tissue grafts contains the coating. The method also includes arranging a magnet over the magnetic coating to induce the plurality of micro tissue grafts to organize in a desired orientation, forming a tissue construct containing the plurality of micro tissue grafts arranged in the desired orientation, and applying the tissue construct to a recipient site.

23 Claims, 10 Drawing Sheets

(51) Int. Cl.

| | | |
|---|---|---|
| *A61L 27/36* | (2006.01) | |
| *A61L 27/44* | (2006.01) | |
| *A61L 27/60* | (2006.01) | |
| *A61M 35/00* | (2006.01) | |
| *A61B 17/00* | (2006.01) | |

(52) U.S. Cl.
     CPC ............. *A61L 27/362* (2013.01); *A61L 27/60* (2013.01); *A61M 35/00* (2013.01); *A61B 2017/00876* (2013.01); *A61B 2017/00969* (2013.01); *A61B 2017/3225* (2013.01); *A61M 2202/09* (2013.01); *A61M 2205/0288* (2013.01)

(58) Field of Classification Search
     USPC .......................................................... 600/36
     See application file for complete search history.

(56)                      References Cited

U.S. PATENT DOCUMENTS

| | | | | |
|---|---|---|---|---|
| 4,773,418 | A | 9/1988 | Hettich | |
| 6,544,762 | B1 | 4/2003 | Tranquillo | |
| 9,060,803 | B2 | 6/2015 | Anderson | |
| 11,065,031 | B2 * | 7/2021 | Anderson | A61B 17/322 |
| | | | | 606/132 |
| 2004/0175690 | A1 | 9/2004 | Mishra | |
| 2005/0020506 | A1 | 1/2005 | Drapeau | |
| 2011/0264115 | A1 | 10/2011 | Asrani et al. | |
| 2011/0313429 | A1 | 12/2011 | Anderson | |
| 2012/0035618 | A1 | 2/2012 | Sabir | |
| 2012/0035619 | A1 | 2/2012 | Sabir et al. | |
| 2012/0197267 | A1 | 8/2012 | Sabir et al. | |
| 2012/0271320 | A1 | 10/2012 | Hall | |
| 2015/0127116 | A1 | 5/2015 | Pringle | |
| 2015/0216545 | A1 | 8/2015 | Anderson | |
| 2015/0328381 | A1 | 11/2015 | Swain | |
| 2016/0166732 | A1 | 6/2016 | Tumey | |
| 2016/0184245 | A1 | 6/2016 | Eberting | |
| 2016/0296663 | A1 | 10/2016 | Higley | |
| 2016/0310157 | A1 | 10/2016 | Guiles | |
| 2018/0140316 | A1 | 5/2018 | Anderson | |
| 2019/0269430 | A1 | 9/2019 | Anderson | |

FOREIGN PATENT DOCUMENTS

| | | | | |
|---|---|---|---|---|
| WO | WO-2010003062 | A2 * | 1/2010 | ............ A61L 27/54 |
| WO | 2011140497 | A2 | 11/2011 | |
| WO | 2015051164 | A2 | 4/2015 | |
| WO | 2016127091 | A1 | 8/2016 | |
| WO | 2016164890 | A1 | 10/2016 | |
| WO | 2018081707 | A1 | 5/2018 | |

OTHER PUBLICATIONS

European Patent Office, Extended Search Report, Application No. 22209567.1, Mar. 13, 2023, 10 pages.
European Patent Office, Extended European Search Report for application 17864294.8. Mailed on May 7, 2020.
Gach, P. C., et al. "Transparent magnetic photoresists for bioanalytical applications." Biomaterials 31.33 (2010): 8810-8817.
International Searching Authority, International Search Report and Written Opinion for application PCT/US2017/059035, mailed on Jan. 5, 2018, 13 pages.
International Searching Authority, International Search Report and Written Opinion for application PCT/US2020/030707, mailed on Aug. 6, 2020, 10 pages.
Kobayashi, N., et al. "Optically transparent ferromagnetic nanogranular films with tunable transmittance." Scientific reports 6 (2016): 34227.
Tam, J., et al. "Fractional skin harvesting: autologous skin grafting without donor-site morbidity." Plastic and Reconstructive Surgery Global Open 1.6 (2013).
Ziolo, R. F., et al. "Matrix-mediated synthesis of nanocrystalline ?-Fe2O3: a new optically transparent magnetic material." Science 257.5067 (1992): 219-223.

* cited by examiner

20

22

HARVEST MICRO TISSUE
COLUMNS FROM DONOR
SITE

24

ARRANGE MICRO TISSUE
COLUMNS IN DESIRED
ORIENTATION

26

APPLY MICRO TISSUE
COLUMNS TO RECIPIENT
SITE

112 — REPLACE NEEDLES IN HARVESTING ARRAY WITH APPLICATORS

114 — PRE-TREAT DONOR SITE WITHIN HARVESTING AREAS USING APPLICATOR ARRAY

116 — REPLACE APPLICATORS WITH NEEDLES

118 — HARVEST MTCS FROM DONOR SITE

Top view of donor site:

Tissue cutting boundary 100

Magnetic adhesive 40

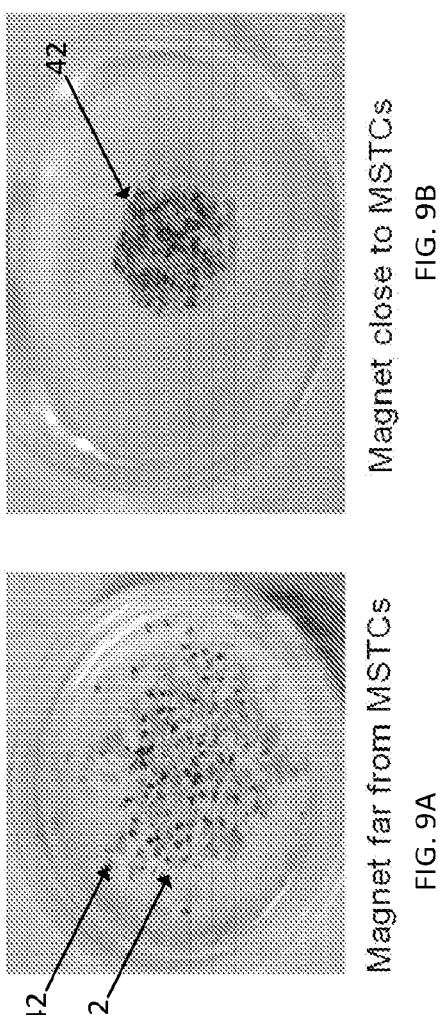
Magnet far from MSTCs
FIG. 9A
Magnet close to MSTCs
FIG. 9B
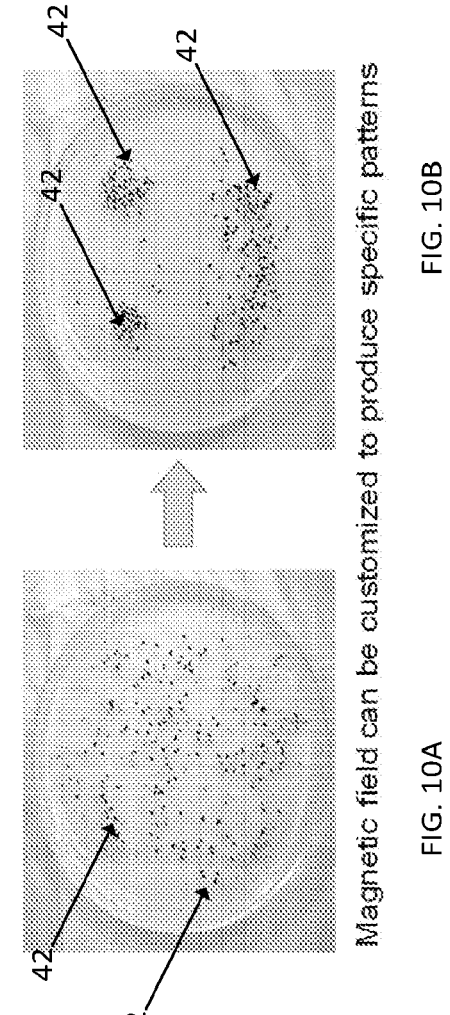
FIG. 10A
Magnetic field can be customized to produce specific patterns
FIG. 10B After 1 week under compression dressing, construct is still intact Skin construct with oriented and assembled MSTCs, in porcine excision wound

SYSTEMS AND METHODS FOR MAGNET-INDUCED ASSEMBLY TISSUE GRAFTS

CROSS-REFERENCE TO RELATED APPLICATIONS

This application is a U.S. National Phase of PCT Application No. PCT/US2020/030707 filed on Apr. 30, 2020, which is based on, claims priority to, and incorporates herein by reference in its entirety, U.S. Provisional Patent Application Ser. No. 62/840,728, filed on Apr. 30, 2019.

STATEMENT REGARDING FEDERALLY FUNDED RESEARCH

This invention was made with government support under HU0001-17-2-0009 awarded by the Military Medicine Technology Transformation Collaborative. The government has certain rights in the invention.

BACKGROUND

Autologous skin grafting is the current "gold standard" for repairing wounds that cannot be closed by primary or secondary intention. More specifically, an autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery, and birth defects. Generally, grafting procedures can be limited by the amount of tissue that can be removed from the donor site without causing excessive adverse effects. More specifically, availability of tissue for autografting can be limited by a total area of tissue needed, healing behavior of the donor site, similarity of the donor and recipient sites, aesthetic considerations, and/or other characteristics of candidate donor and/or recipient sites.

A sheet graft is one type of autograft and refers to a piece of tissue that is removed, or harvested, from an undamaged donor site. For example, a sheet graft may be obtained using an instrument structured to gently shave a piece of tissue from the skin at the donor site. The size of the donor skin piece used for the graft may be about the same size as the damaged recipient site, slightly larger than the recipient site (e.g., to account for potential shrinkage of the graft tissue after harvesting), or smaller than the recipient site (e.g., with grafts that can be meshed and expanded). Once harvested, the sheet graft can be applied over the recipient site wound, stapled or otherwise fastened in place, and allowed to heal.

Sheet grafts can be full-thickness or split-thickness. For example, a conventional split-thickness graft can be formed by harvesting a sheet of epidermis and upper dermal tissue from a donor site (leaving the deeper dermal portions remaining in the donor site), whereas full-thickness skin grafts can be formed using both the epidermis layer and the entire dermal layer. The type of sheet graft used can affect healing at both the donor site and the recipient site.

For example, in conventional split-thickness grafts, the skin tissue may grow back at the donor site in a process similar to that of healing a second-degree burn. Split-thickness grafts may thus be preferable to full-thickness grafts because the donor site can at least partially recover on its own, albeit often with scarring, pain, and other long-term side effects. However, skin tissue removed from the donor site for a split-thickness skin autograft generally includes only a thin epithelial layer, which can lack certain elements of the dermis that would improve structural stability and normal appearance at the recipient site once healed. Thus, split-thickness grafts are more broadly applicable, but the lack of deep dermal structures in these grafts means that they are unable to fully restore normal skin structure or function, leading to significant post-graft scarring at the recipient site and often long-term pain and scarring at the donor site.

In conventional full-thickness grafts, more characteristics of normal skin, such as color, texture, and thickness, can be maintained at the recipient site following the grafting procedure (i.e., because the dermal component can be preserved in such grafts). For example, full-thickness grafts can contain a greater collagen content, dermal vascular plexus, and epithelial appendages as compared to split-thickness grafts. Full-thickness grafts may also undergo less contraction while healing. These properties can be important on more visible skin areas, such as the face and hands. Additionally, hair can be more likely to grow from full-thickness grafts than from split-thickness grafts, and sweat glands and sebaceous glands can be more likely to regenerate in full-thickness grafts than in split-thickness grafts, taking on the sweating characteristics of the recipient site.

While full-thickness grafts can provide improved tissue quality at the recipient site, the donor site is completely sacrificed because there is no dermis left for skin to regenerate from. Thus, there is a very limited availability of potential donor sites, and donor sites for full-thickness grafts must be surgically closed. Additionally, full-thickness grafts require more precise conditions for survival because of the greater amount of tissue requiring revascularization. As such, conventional full-thickness skin grafts are generally limited to relatively small, uncontaminated, well-vascularized wounds, and may not be appropriate for as many types of graft procedures as split-thickness grafts.

Furthermore, various engineered "skin substitutes" have been developed in attempt to circumvent the above donor site issues associated with autografts. However, such attempts have not been able to recapitulate the complex composition and architecture of natural skin, and are costly to produce. As a result, skin substitutes have not been able to replace autografts as the corner stone of wound repair.

In light of the above, it may be desirable to provide systems and methods for tissue harvesting and grafting that provide efficient graft tissue with minimal donor site scarring while also properly replicating normal tissue microanatomy at the recipient site. Additionally, it is desirable for such systems and methods to be scalable for use at recipient sites of various sizes and shapes.

SUMMARY

The systems and methods of the present disclosure overcome the above and other drawbacks by providing fractional tissue grafts, in the form of full-thickness micro tissue columns, in a tissue construct that maintains a desired orientation of the individual tissue columns, such as a substantially vertical, epidermal-dermal orientation. Magnet-induced self-assembly of the tissue columns provides a rapid and scalable method for proper assembly in the desired orientation.

In accordance with one aspect of the disclosure, a method for assembling a plurality of micro tissue grafts is provided. The method can include applying a magnetic coating over a surface of a donor site and harvesting the plurality of micro tissue grafts from the donor site, so that an upper surface of each of the plurality of micro tissue grafts contains the coating. The method can also include arranging a magnet over the magnetic coating to induce the plurality of micro tissue grafts to organize in a desired orientation, forming a tissue construct containing the plurality of micro tissue grafts arranged in the desired orientation, and applying the tissue construct to a recipient site.

In accordance with another aspect of the disclosure, a method for assembling a plurality of micro tissue grafts using magnetic assistance is provided. The method can include replacing needles of a needle harvesting array with coating applicators and applying a magnetic coating to harvesting areas of a donor site using the coating applicators. The method can also include replacing the coating applicators within the needle harvesting array with the needles and harvesting the plurality of micro tissue grafts from each of the harvesting areas so that an upper surface of each of the plurality of micro tissue grafts contains the coating. The method can further include arranging a magnet over the magnetic coating to induce the plurality of micro tissue grafts to organize in a desired orientation, forming a tissue construct containing the plurality of micro tissue grafts arranged in the desired orientation, and applying the tissue construct to a recipient site.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 5A and 5B illustrate perspective views of tissue grafts, FIG. 5C illustrates a top-down view of a tissue graft construct, and FIG. 5D illustrates a side view of the tissue graft construct.

FIGS. 9A and 9B are top-down views of tissue grafts assembled using a magnetic coating technique with varying magnetic distances from the grafts.

FIGS. 10A and 10B are top-down views of tissue grafts assembled using a magnetic coating technique with varying magnetic fields.

FIG. 11A illustrates the wound at time zero upon receiving the graft and FIG. 11B illustrates the wound one week after time zero while under compression dressing.

FIG. 13A illustrates histology results one week after treatment and FIG. 13B illustrates histology results two weeks after treatment. The scale bars in FIGS. 13A-13B are 1 millimeter.

DETAILED DESCRIPTION

The disclosure provides systems and methods for organizing and assembling tissue grafts with magnetic assistance. More specifically, the present systems and methods enable magnet-induced assembly of multiple micro tissue grafts, in the form of biological micro tissue columns, into a larger tissue construct in a way that maintains a desired orientation of the individual tissue columns.

Figure 1:
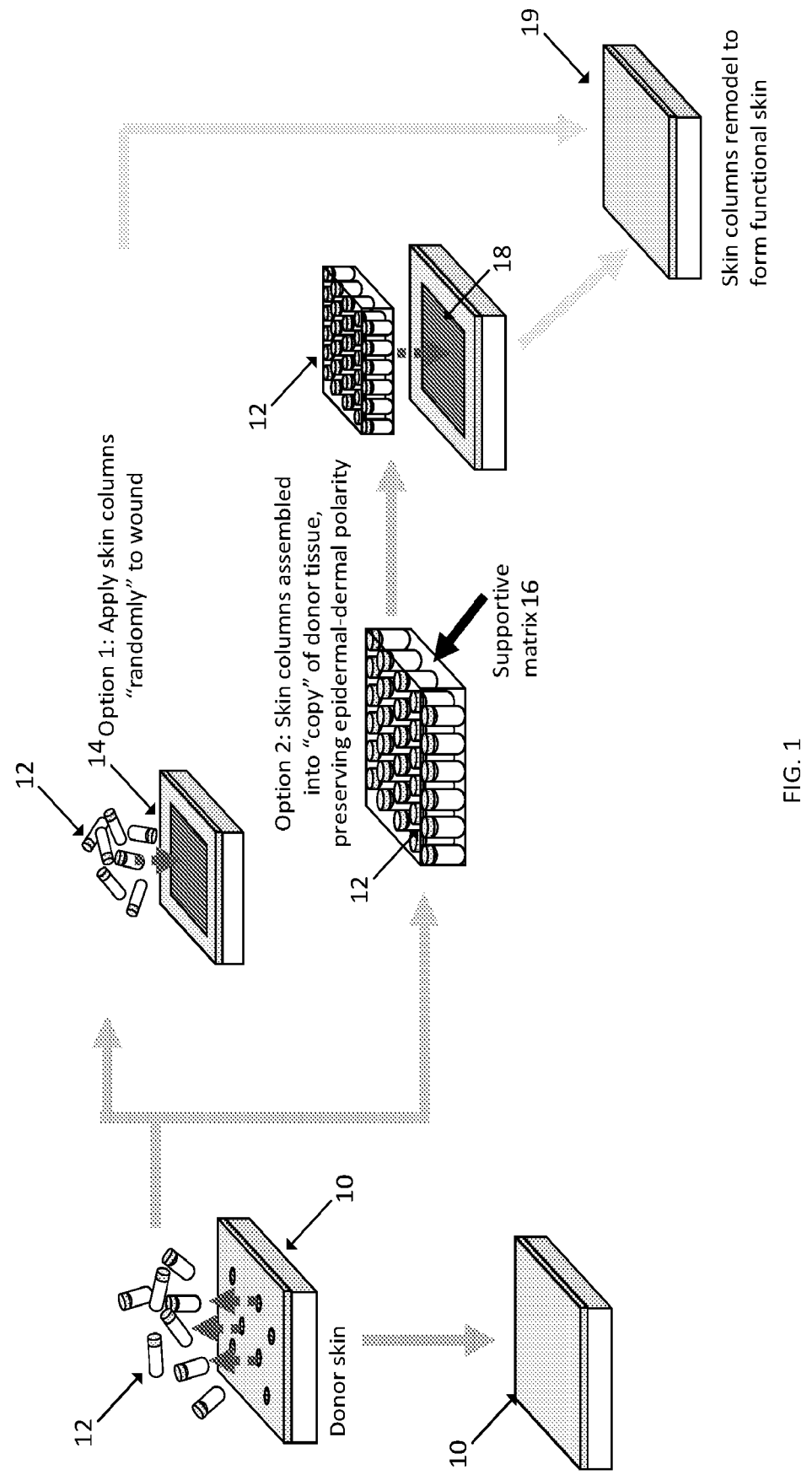
FIG. 1 is a diagram illustrating methods for organizing and assembling tissue grafts.

For example, as shown in FIG. 1, full-thickness skin tissue can be harvested from a donor site 10 in the form of small columns 12 (e.g., several hundred micrometers in diameter). The small size of these micro tissue columns (MTCs) 12 can allow donor sites 10 to heal quickly without long-term morbidity or scarring. According to a first method, these micro tissue columns 12 can be applied to a wound bed 14 as "random" fractional grafts to accelerate wound healing and reduce contraction. That is, the micro tissue columns 12 are applied to the wound bed 14 randomly, in no particular orientation. However, because skin is naturally polarized in architecture, engrafting micro tissue columns as an array having a proper epidermal-dermal orientation into the wound bed can further improve and accelerate healing by accelerating re-epithelialization processing, recapitulating normal dermal architecture, and reducing scarring. As such, the methods and systems disclosed herein facilitate the orientation of micro tissue columns 12, and enable their assembly into three-dimensional, full-thickness constructs 16 to be applied to a wound bed 18, as further shown in FIG. 1. As a result, following application to the wound bed 18, the micro tissue columns 12 can remodel to form functional skin 19. The present systems and methods also provide a practical, scalable solution for using large numbers of micro tissue columns to improve healing wounds of various sizes and shapes with minimal or no scarring at donor sites.

Figure 2:
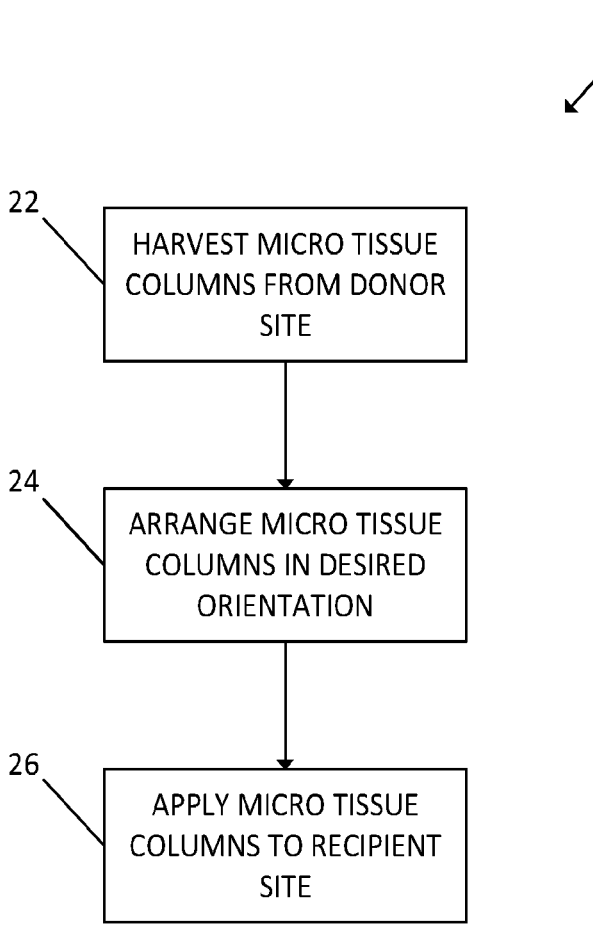
FIG. 2 is a flow diagram illustrating a method for organizing and assembling tissue grafts.

Accordingly, FIG. 2 illustrates a method 20 for assembling micro tissue columns in accordance with the present disclosure. Generally, as shown in FIG. 2, MTCs are harvested from a donor site at step 22. At step 24, some or all MTCs are arranged in a desired orientation (e.g., matching an epidermal-dermal polarity of normal skin). And at step 26, the oriented MTCs are applied to a recipient site. While the term micro tissue columns, or MTCs, is used herein, it should be noted that this term may be interchangeable with micro tissue grafts or micrografts. Furthermore, when the subject tissue is skin, MTCs may be referred to as micro skin tissue columns (MSTCs).

Referring now to step 22 of FIG. 2, the MTCs can be harvested from a donor site. More specifically, MTCs can be formed by removing elongated, substantially cylindrical portions of tissue from the donor site, thus leaving holes therein. In some embodiments, a diameter or width of an MTC can be less than about 2 millimeters (mm) or less than about 1 mm. In some embodiments, the diameter or width can be less than about 0.5 mm, less than about 0.3 mm, or about 0.2 mm. In further embodiments, the diameter or width can be between about 0.8 mm and 0.3 mm. In other embodiments, the diameter or width can be between about 0.7 mm and 0.2 mm.

Each MTC can be a full-thickness graft, that is, including both epidermal tissue and dermal tissue from the donor site. In general, it can be preferable to harvest MTCs with epidermal tissue and dermal tissue while avoiding a significant amount of subcutaneous tissue or muscle tissue. In some applications, however, MTCs can further include some subcutaneous fat tissue and/or muscle tissue. For example, each MTC can be about 3 mm in height, which can correspond to a total depth of a typical skin layer (e.g., including both epidermal and dermal layers, where the dermal layer includes hair follicles and sweat or sebaceous glands). A different height may be used, such as between about 2 mm and about 8 mm, based on the particular skin or tissue characteristics of the donor site. Additionally, MTCs can include stem cells throughout the dermal tissue (e.g., stem cells associated with hair follicles and sweat glands and/or stem cells in a lower portion of the dermal layer, for example, near a dermal/fatty layer boundary).

Generally, MTCs can be harvested from the donor site in a way that minimizes or prevents scarring at the donor site. For example, a size of a donor site hole created by a respective MTC can be selected so that the minor damage created heals rapidly and/or without scarring. More specifically, each donor site hole can be small enough to heal quickly by regeneration, that is, by replacement of the harvested tissue volume with new skin tissue that is normal in both structure and function, without or with minimal scarring. Additionally, the size of the donor site holes created by the MTCs can be selected based on creating portions of tissue that can be small enough to promote viability when transplanted or placed in a growth medium, and large enough to form a sufficient amount of graft tissue and/or to capture tissue structures that may be present in the donor tissue.

In some embodiments, a fraction of surface tissue removed from the donor site (which can correspond to a fractional surface area of the donor site occupied by the holes) can be less than about 70%, less than or equal to about 50%, or more preferably between about 10% and about 30%. The fraction of tissue removed can be sufficiently large to provide enough harvested MTCs to form an appropriately sized graft, but small enough to facilitate rapid healing at the donor site based on growth from the remaining undamaged tissue. Other fractions of tissue can be removed from a donor site depending on factors such as, for example, the particular characteristics of the donor site, the size of the graft needed, and the overall amount of donor site tissue available.

According to some embodiments, the MTCs can be harvested using one or more harvesting needles. In some embodiments, harvesting needles can be, but are not limited to, 17-gauge coring needles, 19-gauge coring needles, 22-gauge coring needles, or 25-gauge coring needles. Furthermore, in some embodiments, the harvesting needles may be double-pointed hypodermic needles. However, needles of different types or sizes, individually or grouped in arrays, may be contemplated within the scope of this disclosure. For example, MTCs may be harvested using any of the tools and methods described in U.S. Pat. No. 9,060,803, the entire contents of which is incorporated herein by reference.

The result of step 22 is a fractional skin graft that includes a plurality of harvested MTCs. Furthermore, rather than a single, large donor site wound, the fractional skin grafting techniques described above create minor donor site wounds that can heal with minimal to no scarring.

Additionally, in some embodiments, step 22 can include pre-treating the donor site, such as with a magnetic coating (for example, a magnetic paint or iron oxide particles), as further described below, before or after harvesting to assist MTC orientation at step 24.

Referring now to step 24 of FIG. 2, the harvested MTCs are assembled in a desired orientation, for example, matching an epidermal-dermal polarity of normal skin. More specifically, at step 24, the MTCs can be assembled into a three-dimensional, full-thickness construct maintaining proper epidermal-dermal, substantially vertical orientation. According to some embodiments, step 24 can be accomplished using an external magnet causing the magnetic coating on the surface of each tissue column to orient along magnetic field lines (and, thus, in the desired orientation). Furthermore, in some embodiments, supportive matrix materials can help maintain the overall structure and desired orientation of the assembled tissue columns after the magnetic field is removed, forming a construct of MTCs and matrix. For example, a supportive matrix material can be first introduced in liquid form to permit the MTCs to be properly assembled, then induced to solidify around the assembled tissue columns. That is, harvested MTCs can be submerged in a solution (such as saline, a biocompatible matrix, a collagen solution, or another supportive biomaterial, as further described below), an external magnet can be used to orient the MTCs within the solution, and then the solution (or a different solution) can be induced to solidify to bind the MTCs in place. In another example, a supportive matrix material can be used in solid form and combined with oriented MTCs in layers or rolls.

The following paragraphs and FIGS. 3-10B describe and illustrate example coating and orienting processes in accordance with some embodiments. These processes may encompass steps 22, 24, and/or 26 of FIG. 2.

Figure 3:
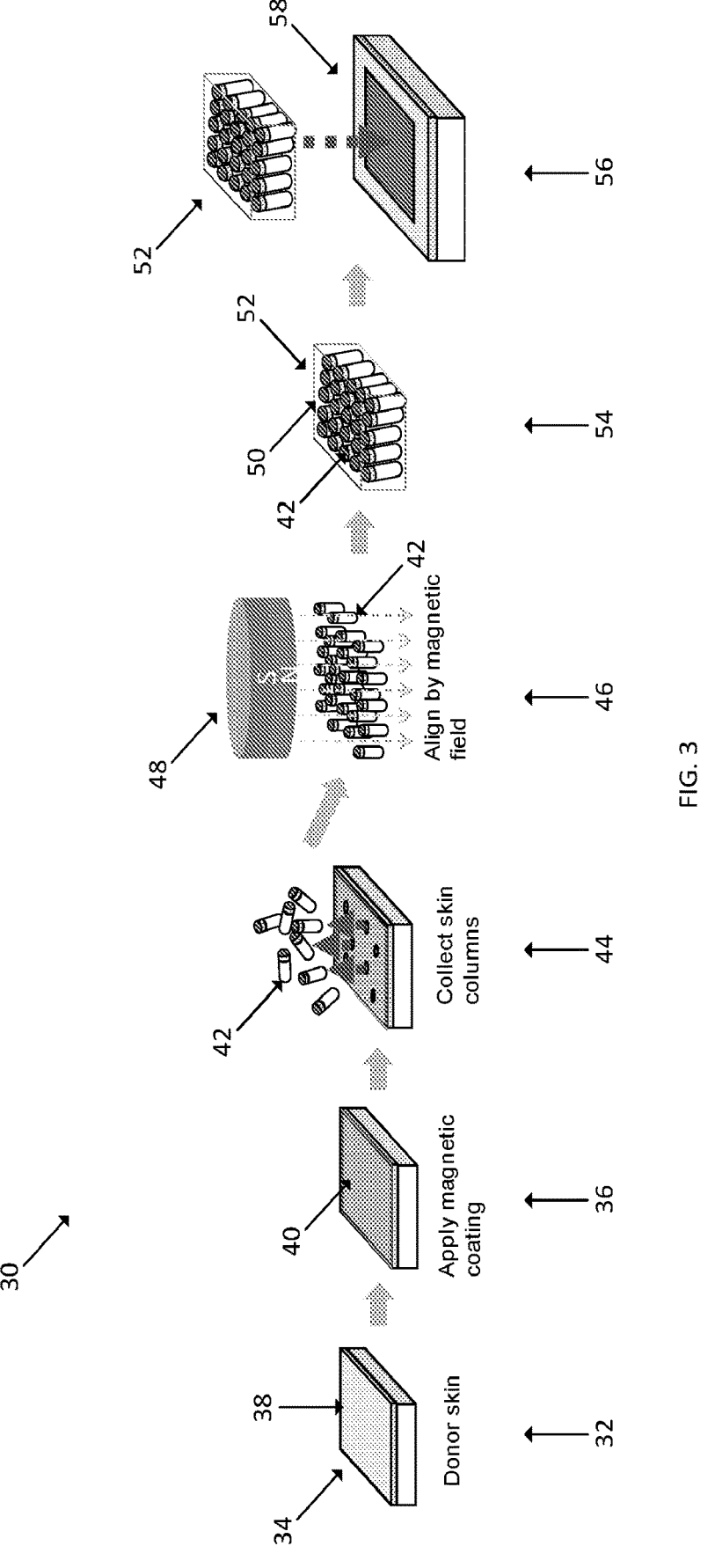
FIG. 3 is a diagram illustrating a magnetic coating technique for orienting tissue grafts.

More specifically, FIG. 3 illustrates an example process 30 according to some embodiments. As shown in FIG. 3, at step 32, a donor site 34 can be selected. At step 36, a surface 38 of the donor site 34 can be coated with a magnetic or ferromagnetic coating 40. Once coated, at step 44, MTCs 42 can be extracted from the donor site 34, for example, in accordance with step 22 described above with respect to FIG. 2. At step 46, the collected MTCs 42 can be aligned in an epidermal-dermal orientation using an external magnet 48. That is, due to the properties of the coating 40, the coated epidermis of some or all MTCs 42 will spontaneously align with the external magnetic field, resulting in the MTCs 42 orienting themselves in the epidermal-dermal orientation. Once aligned, the MTCs 42 can be embedded in a supportive matrix 50 to create a full-thickness skin construct 52 at step 54. At step 56, the construct 52 can be applied to a wound 58 (that is, in accordance with step 26 of FIG. 2).

Figures 4, 5A, 5B, 5C, 5D:
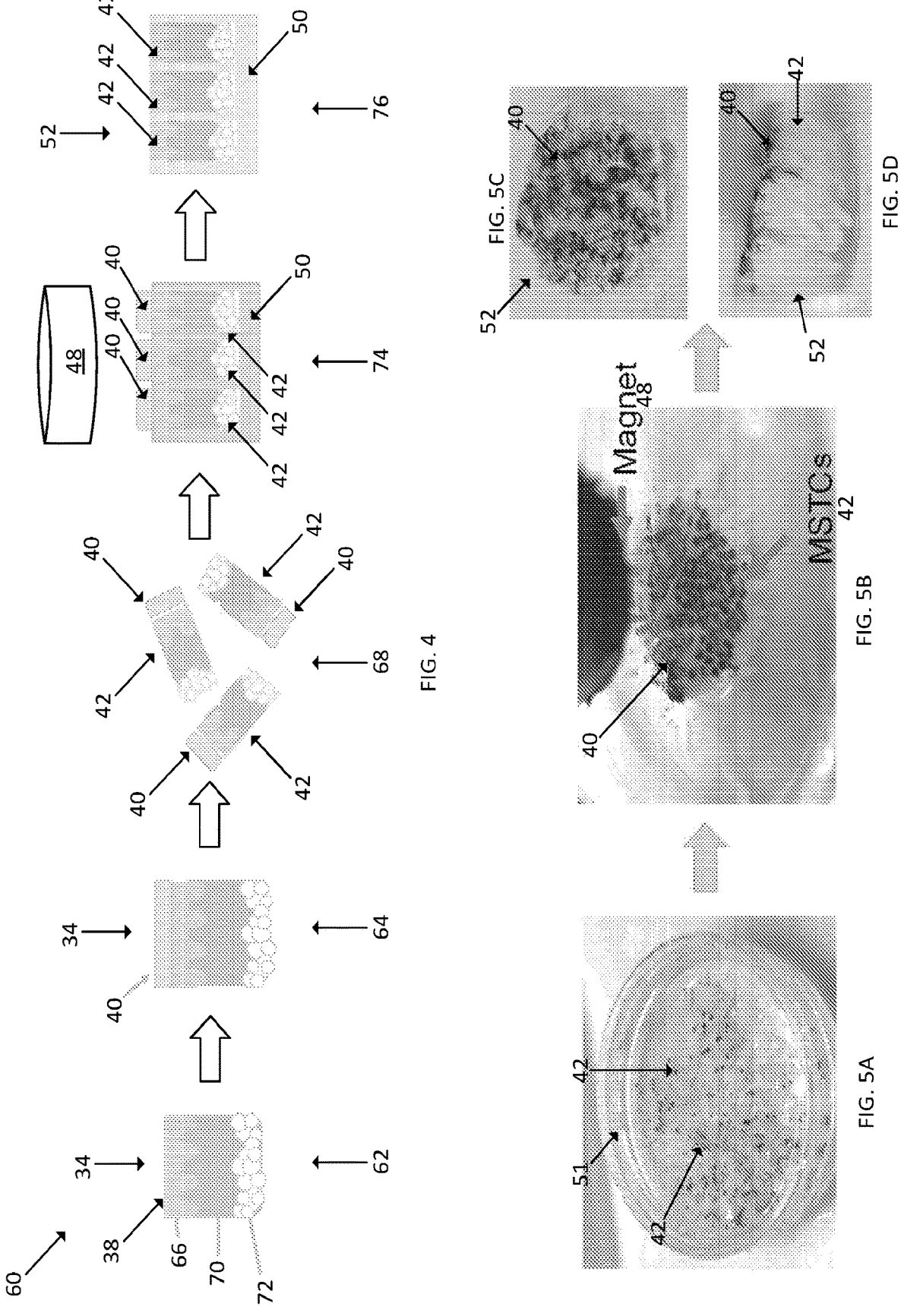
FIG. 4 is a diagram illustrating another magnetic coating technique for orienting tissue grafts.
FIGS. 5A-5D are views of are views of tissue grafts in a solution at various steps of the technique illustrated in FIG. 4, where

FIGS. 4 and 5 illustrate another example coating process 60 according to some embodiments. As shown in FIGS. 4 and 5, at step 62, a donor site 34 can be selected. At step 64, a magnetic coating 40 can be applied to a surface 38 of the donor site 34 (for example, over an epidermal layer 66 of the donor site). At step 68, MTCs 42 are harvested from the donor site 34 in accordance with step 22 described above. For example, the MTCs 42 can be full-thickness grafts, including the epidermal layer 66 as well as a dermal layer 70 and, optionally, a portion of a dermal/fatty layer boundary 72.

At step 74, the MTCs 42 are placed in a solution of supportive matrix material 50 and exposed to a magnetic source 48. For example, FIG. 5A shows harvested MTCs 42 in a solution 50 (in a dish 51) with the magnetic coating 40, shown as a dark coating, on the surfaces 38. Due to the magnetic properties of the coating 40, the coated epidermis 66 of some or all MTCs 42 will spontaneously align generally vertically within the solution 50 in an epidermal-dermal orientation, as shown in FIGS. 4 and 5B.

At step 76, the solution 50 is induced to solidify around the assembled MTCs 42 to create a construct 52 of oriented MTCs 42. Alternatively, in some embodiments, the MTCs 42 may be initially oriented in a different solution, such as saline, and then the oriented MTCs 42 may be embedded in the supportive matrix material 50 to form the construct 52. Once the construct 52 is formed, as shown in FIG. 5C (illustrating a top-down view of the construct 52) and FIG. 5D (illustrating a side view of the construct 52), MTC orientation and structure are maintained without an external magnetic field, as a result of the solidified matrix material 50. Additionally, as shown at step 76 of FIG. 4, in some embodiments, once the construct 52 is solidified, the magnetic coating 40 may be partially or completed removed, as further described below.

Figure 6:
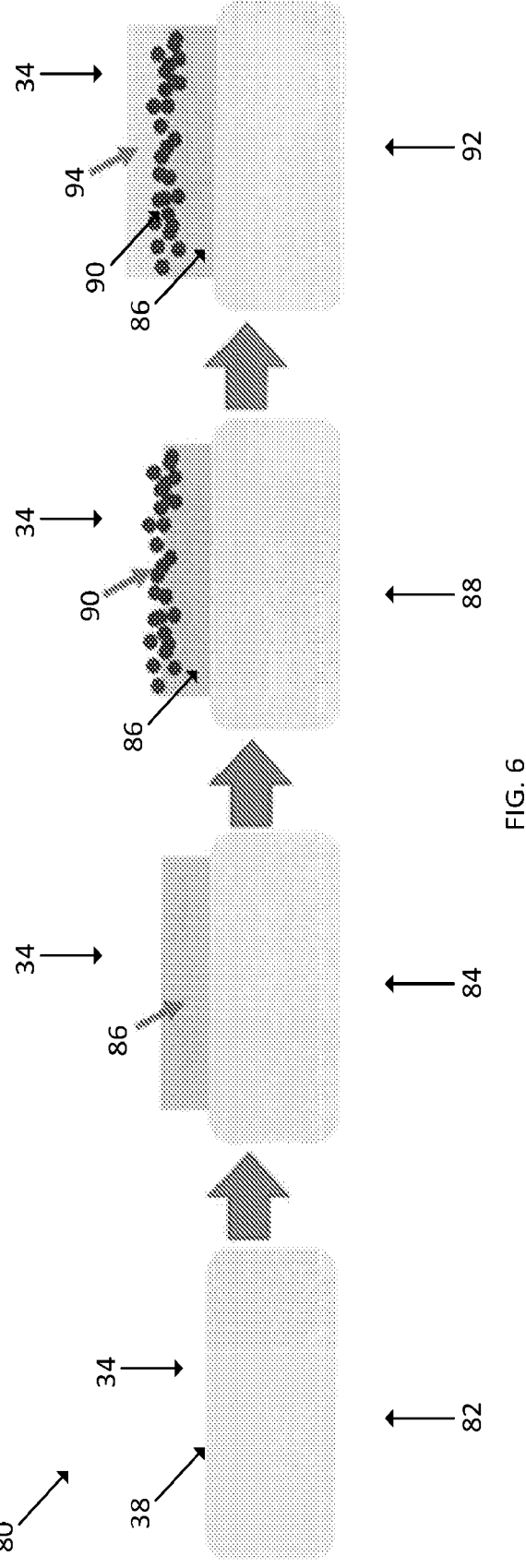
FIG. 6 is a diagram illustrating yet another magnetic coating technique for orienting tissue grafts.

FIG. 6 illustrates yet another example coating process 80. As shown in FIG. 6, at step 82, a donor site 34 can be selected. At step 84, an adhesive coating 86, such as ostomy glue or another suitable adhesive, can be applied to a surface 38 of the donor site 34. At step 88, magnetic (e.g., iron oxide) particles 90 are applied to the adhesive 86. At step 92, an additional coating 94, such as a spray-on bandage, is applied over the magnetic particles 90. While not shown in FIG. 6, following step 92, MTCs 42 can be harvested from the donor site 34 (e.g., as described above in accordance with step 22) and placed in a solution 50. An external magnet 48 can then be positioned over the solution 50 so that some or all MTCs 42 generally align vertically within the solution 50 in an epidermal-dermal orientation. That is, due to the magnetic properties of the particles 90, the coated epidermis 66 of some or all MTCs 42 will align according to magnetic field lines created by the magnet 48, orienting the epidermis 66 toward the top of the solution 50. The solution 50 is then induced to solidify around the assembled MTCs 42 to create a construct 52 of oriented MTCs 42.

In some embodiments, any of the coating techniques described herein may be combined with an agitation step. For example, agitating the solution 50 can help stir MTCs 42 that may have sunk down into the solution 50, increasing their chances of floating up toward the fluid surface to be closer to the magnetic field. Additionally, agitation can increase the likelihood that MTCs 42 floating at the surface of the solution 50 will get close enough to each other to cluster together (i.e., due to the effects of surface tension around small floating objects, also known as the "Cheerios effect").

Referring back to the method of FIG. 2, once MTCs 42 are harvested and oriented at steps 22 and 24 in accordance with any of the above-described techniques, they are applied to a recipient site (such as a wound 58) at step 26. More specifically, following steps 22 and 24, one or more three-dimensional, full-thickness constructs 52 are available for wound healing, and these constructs 52 include MTCs 42 in substantially vertical, epidermal-dermal orientation. These constructs 52 are three-dimensional because they have a usable width, length, and height and are full-thickness because they include at least epidermal and dermal layers 66, 70. In some embodiments, a construct 52 may be round. However, in other embodiments, constructs may be rectangular, square, or another suitable shape.

Figure 11B:
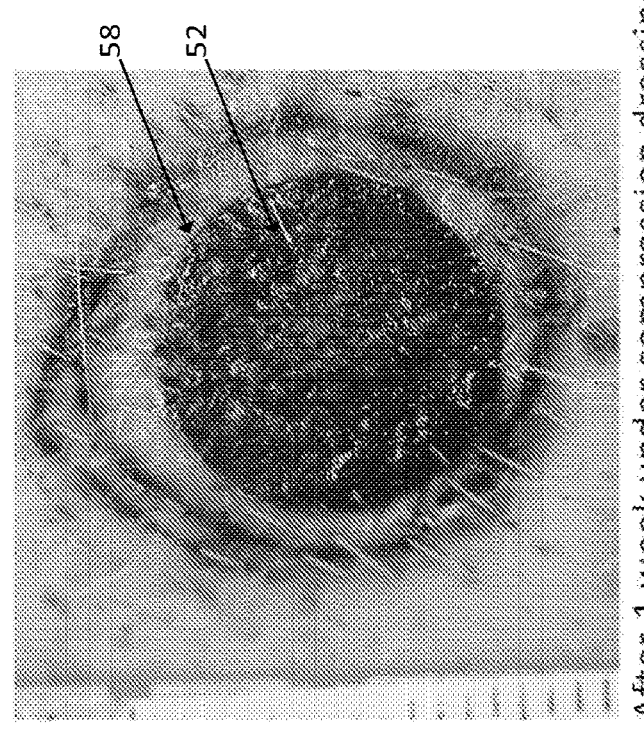
FIGS. 11A-11B illustrate top views of a wound with a tissue graft assembled by a magnetic coating technique, where
Figure 11B:
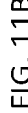
Figure 11A:
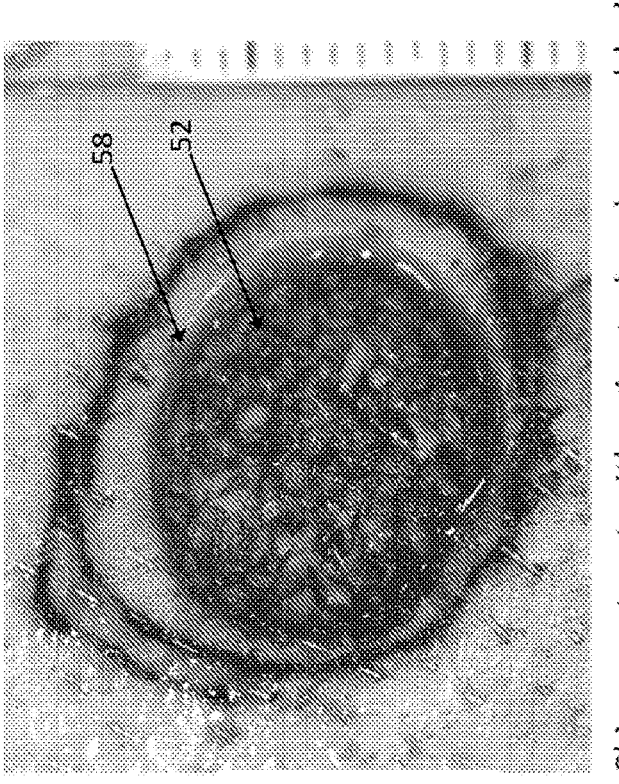

According to step 26, the MTCs 42 can be placed in or on a wound 58 in order to entirely, or at least partially, cover the wound 58. In some embodiments, a single construct 52 may entirely cover a wound 58 at a recipient site, as shown in FIG. 11A. In other embodiments, multiple constructs, each containing a plurality of MTCs 42, can be arranged side-by-side in order to fit the geometry of a wound 58. Accordingly, the present methods can be scalable for use in large and/or asymmetrical wounds 58 by providing one or more solid constructs 52, each formed with a plurality of MTCs 42, to be arranged side-by-side at a recipient site 58. Furthermore, FIG. 11A shows the construct 52 immediately after placement in an excision wound 58. As shown in FIG. 11B, after one week under compression dressing, the construct 52 remained intact, thus facilitating proper epidermal-dermal orientation throughout the healing process.

Regarding the coating 40 in the above examples, a magnetic or ferromagnetic coating can be used to orient MTCs 42. In some embodiments, powdered iron oxide ($Fe_3O_4$) can be mixed with a silicone gel to produce a ferromagnetic coating (e.g., a magnetic paste). Such a coating 40 can remain adhered to the epidermal surface 38 of MTCs 42 throughout the harvesting process. Additionally, other magnetic coatings may be used in some embodiments, such as coatings containing magnetic paint or magnetic particles mixed with other materials.

In some applications, the coating 40 may be allowed to slough off during the natural turnover of the epidermis 66. For example, the magnetic particles in the coating 40 can be relatively small (such as less than 0.5 micrometers) so that they can be cleared by the body. While some particles that enter deeper parts of the tissue during the harvesting procedure may become "tattoos," using smaller particles can facilitate natural removal. For example, permanent tattoo particles are generally around 0.5 to 10 micrometers in size. Using magnetic material that is of dimensions outside the size range that causes permanent tattoos allows for any magnetic material that becomes entrapped under the skin during the harvesting or engraftment processes to be effectively and naturally cleared from the body during tissue turnover. Additionally, in some applications, iron oxide particles of the coating 40 may be substituted with optically transparent magnetic materials so that the sites 34, 58 do not appear "tattooed" by the coating 40.

Furthermore, in some applications, the iron oxide coating 40 may be washed off after the construct 52 is assembled. At assembly, the MTCs 42 are held in place by the solidified supportive matrix material 50, and the coating 40 (and resulting magnetic orientation assistance) is therefore no longer needed. According to one example, the coating 40 may be wiped off the epidermal surface 38. According to another example, the above silicone gel adhesive may be replaced with a material that can liquefy, and thus be easily removed, in response to a trigger, such as a light, chemical, or temperature trigger. Thus, when magnetic assistance is no longer needed, the trigger can be used to liquefy the material, allowing it to be wiped off or otherwise removed from the tissue.

Figure 7:
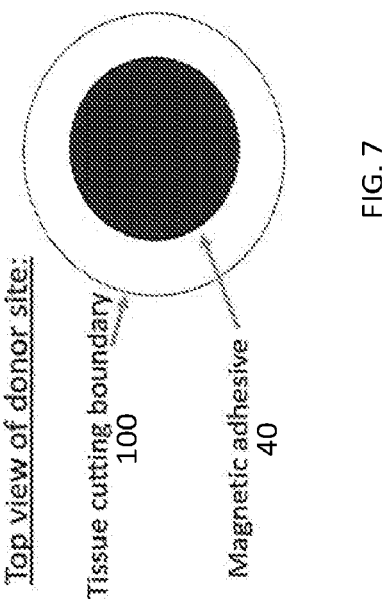
FIG. 7 is a schematic top view of a donor site for a tissue graft in accordance with a magnetic coating technique.

Additionally, in some applications, the coating 40 may not be applied to the entire donor site 34, as shown in FIG. 3, but rather only to the fraction of tissue that will be harvested in order to minimize the application area. For example, as shown in FIG. 7, a "dot" or small circle (or other shape) of magnetic coating 40 can be applied within a tissue cutting boundary 100 of each individual MTC 42. Using this technique, where the coating 40 is smaller than the tissue cutting boundary 100, the coating 40 would not be carried by the harvesting needle into the donor site 34 during harvesting (e.g., when the needle is inserted into the donor site tissue).

Figure 8:
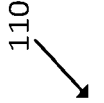
FIG. 8 is a flow diagram illustrating a magnetic coating technique for coating a donor site.
Figure 8:
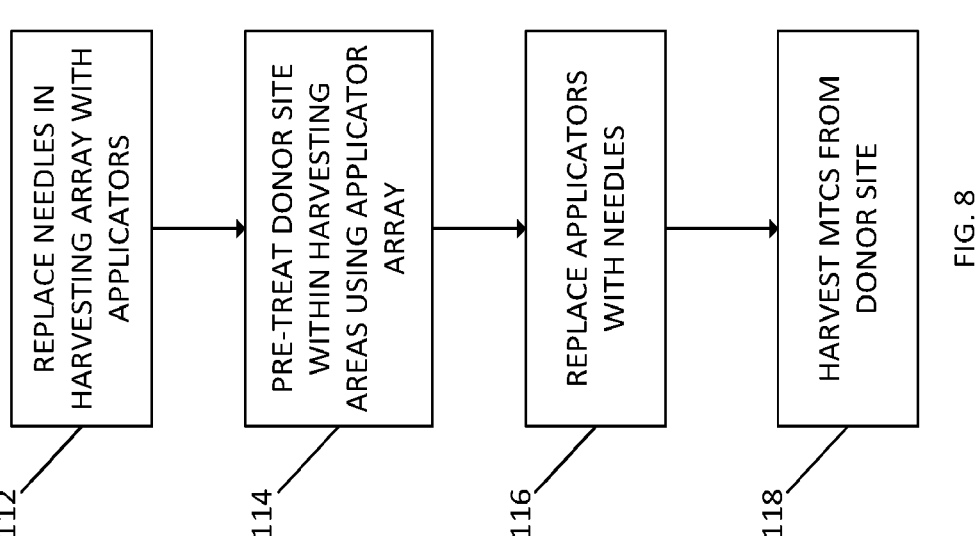

FIG. 8 illustrates an example coating process 110 to accomplish the coating technique illustrated in FIG. 7. For example, at step 112, needles of a harvesting needle array can be replaced with similar-size or smaller-sized coating applicators. That is, the applicator diameter may be equal to or smaller than a diameter of the harvesting needles. At step 114, each individual harvest area of the donor site 34 may be pre-treated with magnetic coating 40 using the applicators. A "harvest area" may be considered the area within the tissue cutting boundary 100 illustrated in FIG. 7. Thus, either the entire harvest area or a portion of the harvest area may be coated at step 114. At step 116, the applicators may be replaced with the harvesting needles. At step 118, MTCs 42 can be harvested from the donor site 34 using the harvesting needle array.

With the magnetic coating 40 applied according to any of the above techniques, an external magnet 48 can be used to control patterning of the MTCs 42 very precisely. That is, the spatial distribution of MTCs 42 can be controlled by the magnetic field. For example, spacing between MTCs 42 in the solution 50 can be controlled by varying the distance between the MTCs 42 and the magnetic source 48. FIG. 9A illustrates a distribution of MTCs 42 farther apart, caused by a magnet 48 further away from the MTCs 42, while FIG. 9B illustrates a distribution of MTCs 42 closer together, caused by a magnet 48 closer to the MTCs 42. Thus, in some embodiments, arranging the magnet 48 to orient the MTCs 42 can include setting a distance between the magnet 48 and the MTCs 42 to achieve a desired relative spatial distribution of MTCs 42.

Furthermore, the magnetic field can be customized to produce specific patterns of MTCs 42. Additionally, in some applications, an array of magnets 48 (that is, rather than a single magnet 48) can be used, for example, to create regions of different patterns or different densities of MTCs 42 within the same tissue construct 52. For example, FIG. 10A illustrates a substantially even distribution of MTCs 42 with a first pattern caused by a first magnetic field setup, while FIG. 10B illustrates a varied distribution of MTCs 42 with a second pattern caused by a second magnetic field setup. Thus, in some embodiments, arranging the magnet 48 to orient the MTCs 42 can include creating a specific magnetic field pattern with the magnet 48 to produce a desired arrangement pattern of MTCs 42.

As described above, supportive matrix materials 50 can be used to orient the MTCs 42 and/or maintain MTC orientation in a construct 52. More specifically, the supportive materials 50 can be used to create a construct 52 that maintains the overall structure and orientation of the assembled tissue columns 42 after the magnetic field is removed. As a result, these constructs 52 create a more easily handled graft and, in some applications, can allow for physicians to add drugs, other components, or other cell types, as needed, to the wound 58 by adding these components to the construct 52.

Generally, the following set of criteria may be used to select a supportive matrix material 50. First, the physical properties of the material 50 are compatible with the overall assembly process, described above. That is, the material 50 may initially be in liquid form that allows MTCs 42 to move freely as they align themselves with the external magnetic field, and then can be induced to solidify within a reasonable timescale for use in a clinical setting. Second, after solidification, the matrix 50 can be mechanically robust enough to withstand the mechanical forces typically present in and around wound areas 58, such as friction and compressive forces due to dressing regimens. Third, the matrix 50 can be biocompatible so that the entire matrix construct 52 may be placed directly into a wound 58 (in accordance with step 26). And the matrix 50 can be degradable within a timescale that encourages cellular outgrowth from MTCs 42 and tissue remodeling to progress during the healing process. An example timescale may be, but is not limited to, two to three weeks.

In some embodiments, the supportive material 50 can be a biocompatible and/or biodegradable polymer capable of solidifying after a time period (e.g., the polymer can solidify a time period after being mixed), or in response to induction (e.g., through application of a cross-linking agent). For example, the material 50 be a supportive biomaterial, such as a biocompatible matrix or collagen solution capable of solidifying after incubation.

Example biocompatible matrices 50 can include, but are not limited to, decellularized tissue (e.g., skin, gut, amnion, or other tissue that has been processed to remove all living cells, so all that's left of the original tissue are the extracellular components), matrices made from natural biomolecules (collagen, fibrin, hyaluronan, etc., used alone or in combination) in various forms (e.g., in a gel or spun into fibers), synthetic materials that are biodegradable and have certain bio-mimicking properties (e.g., biodegradable polymers functionalized with cell adhesion moieties), and/or matrices including collagen, hydrogels, fibrin gels, or carbon scaffolds. Additionally, any of the above examples can include growth factor and/or oxygen concentration enhancing material (e.g., $CaO2$) and/or other substances.

In some applications, the supportive matrix material 50 can include naturally-derived biomaterials, such as fibrin and collagen (type I). Crosslinking reagents such as, but not limited to, ribose, EDC/NHS (1-Ethyl-3-(3-dimethylamino-propyl)-carbodiimide/N-hydroxysuccinimide), or Rose Bengal (with photoactivation) may be used to further strengthen the resulting construct 52. Testing was conducted using combinations of these materials to determine their (1) compatibility with the above assembly methods; (2) mechanical robustness; and (3) physiologic compatibility. More specifically, (1) the orientation and spatial distribution of MTCs 42 in constructs 52 were evaluated by histology and quantified; (2) the ability of the constructs 52 to withstand mechanical forces in a wound environment was verified in an ex vivo model that simulates graft handling and wound dressing procedures; and (3) in vivo evaluation of healing outcomes in a porcine excision wound model was conducted. Table 1 below illustrates the results of this testing:

TABLE 1

Results of Biomaterial Testing for Supportive Matrix Material

| Material | Compatible with Assembly Method | Mechanical Robustness | Physiologic Compatibility |
|---|---|---|---|
| Mebiol ® Thermoreversible Hydrogel | X (MTCs could not align) | — | — |
| Fibrin | ✓ | ✓ | X (exuberant inflammation) |
| Fibrin:Collagen(1:1) | ✓ | ✓ | X (exuberant inflammation) |
| Collagen I | ✓ | X | ✓ |

TABLE 1-continued

Results of Biomaterial Testing for Supportive Matrix Material

| Material | Compatible with Assembly Method | Mechanical Robustness | Physiologic Compatibility |
|---|---|---|---|
| | | (gels fragile, lost many to dressings) | |
| Collagen I + Ribose | ✓ | X | — |
| Collagen I + EDC/NHS | ✓ | ✓ | (testing ongoing) |
| Collagen I + rose Bengal + photoactivation | ✓ | ✓ | (testing ongoing) |

More specifically, fibrin and a fibrin collagen mix (1:1) were each tested. The stiffness and elasticity of the resulting constructs 52 were sufficient, but they each induced an exuberant inflammatory response in vivo. With respect to collagen crosslinked by ribose, there was a slight increase in stiffness at lower ribose concentrations up to 150 millimolar (mM), but the resulting construct 52 was still not strong enough to withstand mechanical stressors associated with wound dressing. Ribose concentrations above 150 mM appeared to interfere with the gelatin process when creating the construct 52, which became very slow and, in some cases, the construct 52 did not gel at all.

With respect to collagen crosslinked by EDC and NHS, various concentrations of EDC/NHS were tested, including: (a) 33 mM/6 mM; (b) 16.5 mM/3 mM; (c) 6.6 mM/1.2 mM; and (d) 3.3 mM/0.6 mM. All crosslinking was done at room temperature and before collagen gelation. All combinations strengthened the resulting gel sufficiently to withstand mechanical stresses associated with routine handling and compressing dressing for wound care, but the lower concentrations (e.g., 6.6 mM/1.2 mM and below) resulted in very slow crosslinking that may be impractical for in vivo use in some applications. However, gelling the collagen at the same time as crosslinking progresses may make these lower crosslinked concentrations practical for those or other applications.

With respect to collagen crosslinked by Rose Bengal with photoactivation, testing was conducted with Rose Bengal concentrations ranging from 0.1 uM to 1 mM. All concentrations resulted in stiffer hydrogels except for 0.1 uM. In one study using a 10 uM Rose Bengal concentration, after collagen gelation, photocrosslinking was performed using a 532 nanometer (nM) laser at 450 milliwatts (mW) and treatment energies of 100 joules per centimeter squared (J/cm$^2$). The higher energy led to a stronger hydrogel but did not achieve the robustness of the EDC/NHS-crosslinked hydrogels.

Accordingly, at least ECD/NHS-crosslinked and Rose Bengal-crosslinked hydrogels appear suitable for use as a supportive matrix material 50 in some applications. However, the other materials described above may also be suitable in some applications using specific concentrations and/or solidifying processes. Additionally, as noted above, other substances (such as, growth factor, oxygen concentration enhancing material (e.g., CaO2), drugs, and/or other substances) may be incorporated into the matrix material 50.

Additionally, while the above examples include creating a construct 52 having MTCs 42 in supportive materials 50, in some embodiments, constructs 52 may include MTCs 42 formed together (in the desired orientation) in another manner. As such, these constructs 52 can include MTCs 42 that are oriented properly for application to a wound bed 58, but not supported by exogenous materials dispersed between MTCs 42. Accordingly, in some embodiments, a solid construct 52 may be formed by a material or tool that maintains MTCs 42 arranged and oriented by contacting or communicating with an upper surface 38 of the MTCs 42. For example, MTCs 42 can be coated with a magnetic layer 40, as described above, and then a magnet 48 can be used to pick up all of the oriented MTCs 42 as a solid construct 52. The MTCs 42 may be picked up from a liquid solution or other harvesting tooling (such as within a needle array). In these applications, once the oriented MTCs 42 are picked up, thus forming the construct 52, the construct 52 may be directly applied to a recipient site 58 (as described above with respect to step 26).

Figure 12:
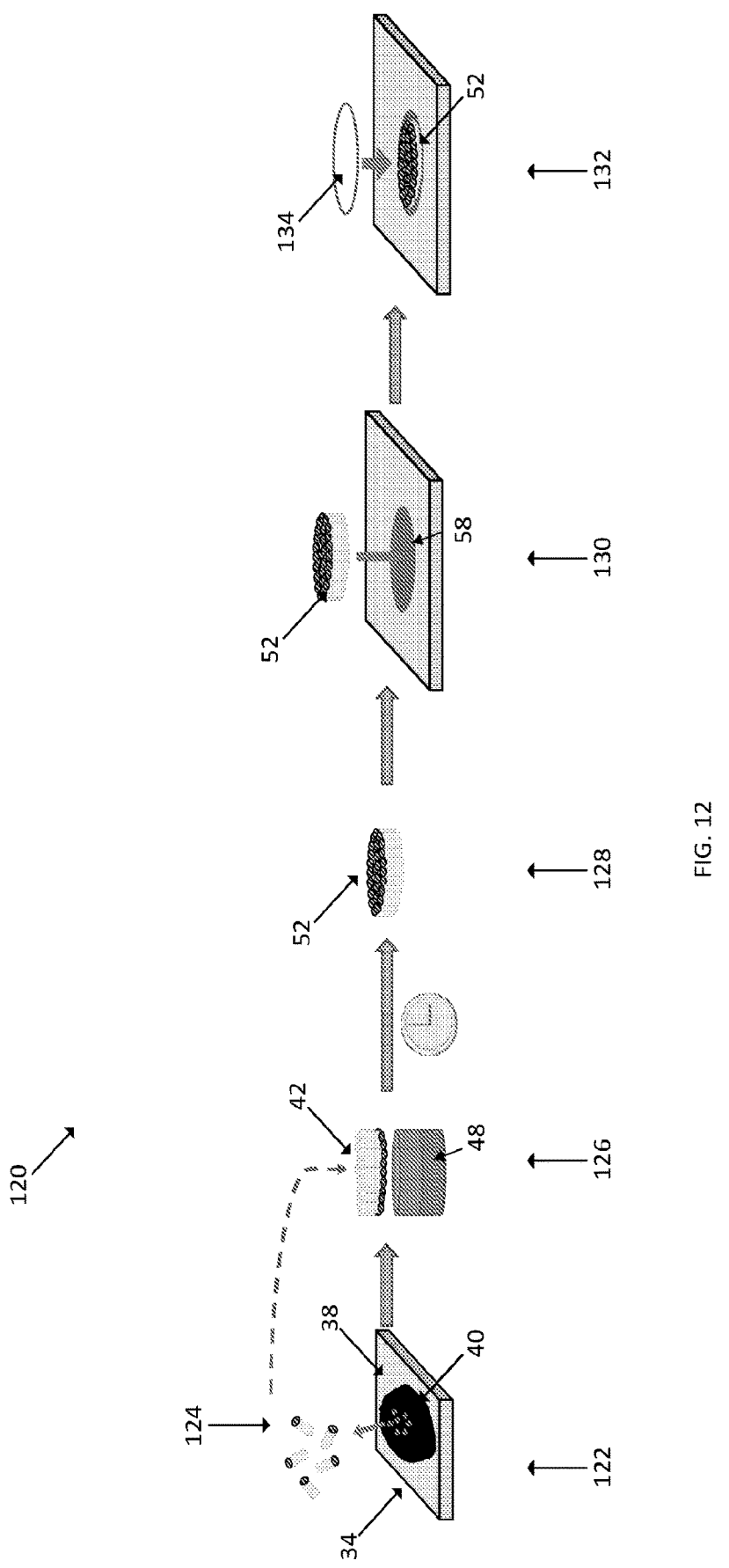
FIG. 12 is a diagram illustrating yet another magnetic coating technique for orienting tissue grafts.

More specifically, according to one example, FIG. 12 illustrates a coating and harvesting process 120. As shown in FIG. 12, at step 122, a surface 38 of a donor site 34 can be coated with a magnetic or ferromagnetic coating 40. Once coated, at step 124, MTCs 42 can be extracted from the donor site 34, for example, in accordance with step 22 described above with respect to FIG. 2. At step 126, the collected MTCs 42 can be aligned in an epidermal-dermal orientation using an external magnet 48. Once aligned, the MTCs 42 can be allowed to dry gently to create a full-thickness skin construct 52, with densely packed, properly-oriented MTCs 42, at step 128. For example, the MTCs 42 can be allowed to air dry for approximately 20 minutes, or another time period. Generally, the MTCs 42 can be dried enough so that they slightly stick together, but not so much that the tissue is desiccated.

Following step 128, at step 130, the construct 52 can be applied to a wound 58 (for example, in accordance with step 26 of FIG. 2). At step 132, an adhesive dressing 134 or tissue adhesive (such as cyanoacrylate glue) can be applied to the top epidermal surface 66 of the construct 52 in order to protect the construct 52 and help keep the MTCs 42 in place. Alternatively, in some embodiments, steps 130 and 132 may be reversed.

Figure 13B:
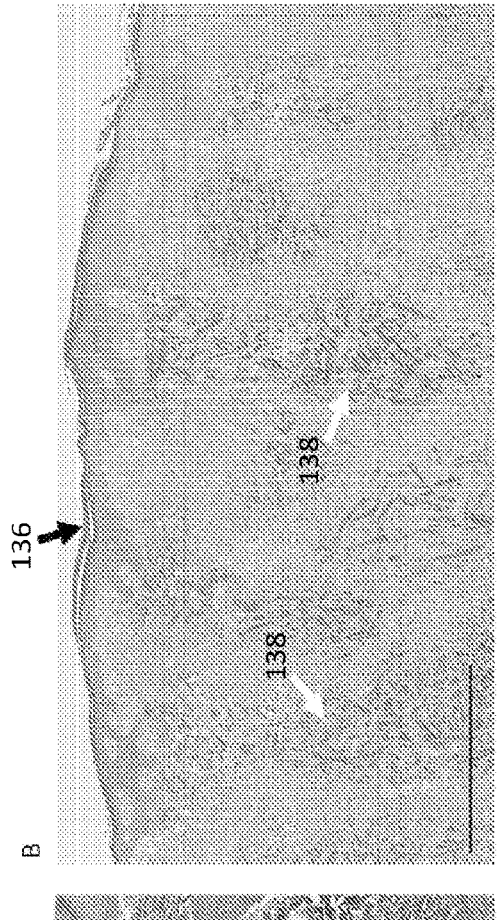
FIGS. 13A-13B illustrate histology results of a porcine full-thickness excision wound treated with tissue grafts oriented in accordance with the technique of FIG. 12, where
Figure 13A:
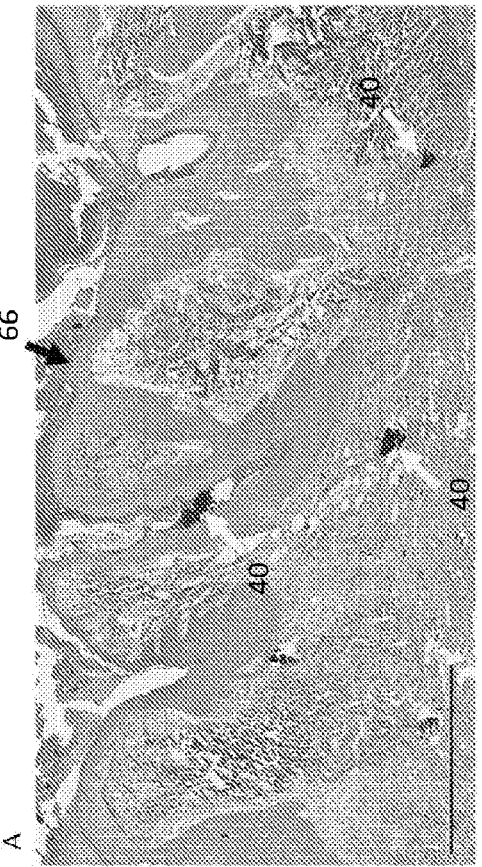

FIGS. 13A and 13B illustrate the results of an experiment conducted using the process 120 of FIG. 12. That is, porcine full-thickness excision wounds were treated with densely packed, oriented MSTCs 42, without supportive biomaterials, in accordance with the process 120 of FIG. 12. FIG. 13A illustrates histology results of the recipient site at one week after treatment, and FIG. 13B illustrates histology results of the recipient site at two weeks after treatment. As shown in FIG. 13A, at one week, a contiguous epidermis 66 is already formed at the skin surface. Furthermore, very little epidermal cells are seen in the dermal compartment 70 of the wound, likely because the MSTCs 42 were oriented properly in the constructs 52. Some iron oxide from the magnetic coating 40 could be seen both in and on top of the wound. As shown in FIG. 13B, at two weeks, the epidermis 66 appears well-formed and mature, with full stratification including stratum corneum 136. In parts of the dermis 70, "basket weave" collagen patterns 138 can be seen. This pattern is characteristic of normal skin, but is absent in scars.

It should be noted that the coating, harvesting, and/or application techniques disclosed herein are not mutually exclusive and one or more techniques may be combined or fully or partially interchanged with other techniques to further increase the total percentage of correctly aligned MTCs 42 and/or achieve desired characteristics. For example, one or more of the above-described techniques may be combined with any one or more techniques described in United States Patent Publication No. 2019/0269430, the entire contents of which is incorporated herein by reference.

In light of the above, the present methods allow for magnet-induced assembly of MTCs, in a desired orientation, into solid, three-dimensional tissue constructs. Furthermore, one or more systems may be provided to fully or partially execute the above-described methods. When such constructs are applied to a recipient site, the full-thickness MTCs can grow, complete with sweat glands and other complex features of the harvested tissue. Accordingly, these MTCs can be used to assist and improve tissue healing at the recipient site (such as a wound). More specifically, properly oriented MTCs can improve healing by accelerating re-epithelialization processing, recapitulating normal dermal architecture, and/or reducing scarring, as compared to healed untreated wounds and healed wounds treated with randomly oriented MTCs.

In particular, while harvested MTCs can be applied to wound beds randomly, that is, without maintaining the normal epidermal-dermal polarity of skin, MTCs organized in a defined epidermal-dermal orientation can be advantageous to accelerate wound healing by providing for more efficient cell and tissue growth and more faithful replication of normal tissue microanatomy (for example, complex structures in full-thickness tissue grafts, like hair follicles, have defined polarities and are generally less tolerant of being implanted in the wrong orientation). Thus, while randomly oriented MTCs have been shown to improve healing compared to untreated wounds (e.g., by healing faster with less contraction), MTCs assembled and oriented in accordance with the systems and methods described above can further improve healing time, contractile response, skin appearance, and/or structural organization.

In light of the above, small columns of full-thickness skin tissue can be harvested, with each donor wound being small enough to heal quickly by regeneration with minimal to no scarring. While such columns can be applied to wound beds randomly to accelerate wound healing, using tissue columns organized in a defined epidermal-dermal orientation can be advantageous by providing for more efficient cell and tissue growth and more faithful replication of normal tissue microanatomy. Furthermore, the above methods and systems for grafting and assembling MTCs are simple and nontoxic, using a varying magnetic field to achieve desired spatial distribution and patterning of MTCs, and using biocompatible supportive materials to form solid constructs that can be used as scalable building blocks capable of properly fitting a desired size and geometry of a recipient site.

The above methods and systems may be used in different wound healing applications, such as, but not limited to, burns, abrasions, and surgical wounds, chronic ulcers such as pressure ulcers, venous leg ulcers, and diabetic foot ulcers, or other grafting applications, such as, but not limited to, vitiligo. Additionally, while the above methods and systems have been described with respect to skin grafts, the principles described herein may applied to other tissue types as well. For example, the above methods and systems may be used with other types of tissue, such as, but not limited to, tissue of the liver, kidney, or heart, to provide micro tissue columns arranged in a desired orientation.

The present invention has been described in terms of one or more preferred embodiments, and it should be appreciated that many equivalents, alternatives, variations, and modifications, aside from those expressly stated, are possible and within the scope of the invention. Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The invention claimed is:

1. A method for assembling a plurality of micro tissue grafts, the method comprising:
   applying a magnetic coating over a surface of a donor site;
   harvesting the plurality of micro tissue grafts from the donor site, using one or more harvesting tools configured to extract small tissue columns, so that an upper surface of each of the plurality of micro tissue grafts contains the coating;
   arranging a magnet over the magnetic coating to induce the plurality of micro tissue grafts to organize in a desired orientation;
   placing the plurality of micro tissue grafts in a supportive material that is in liquid form and inducing the plurality of micro tissue grafts to organize in the desired orientation within the supportive material;
   forming a tissue construct containing the plurality of micro tissue grafts arranged in the desired orientation; and
   applying the tissue construct to a recipient site.

2. The method of claim 1, wherein the magnetic coating includes powdered iron oxide mixed with a silicone gel.

3. The method of claim 2, wherein the powdered iron oxide includes particles less than 0.5 micrometers.

4. The method of claim 1, wherein forming the tissue construct includes inducing the supportive material to solidify around the plurality of micro tissue grafts.

5. The method of claim 4, wherein the supportive material includes collagen crosslinked by EDC (1-Ethyl-3-(3-dimethylaminopropyl)-carbodiimide) and NHS (N-hydroxysuccinimide).

6. The method of claim 4, wherein the supportive material includes collagen crosslinked by Rose Bengal with photo-activation.

7. The method of claim 1 and further comprising agitating the supportive material after placing the plurality of micro tissue grafts in the supportive material.

8. The method of claim 1, wherein arranging the magnet includes setting a distance between the magnet and the plurality of micro tissue grafts to adjust a relative spatial distribution of the micro tissue grafts.

9. The method of claim 1, wherein arranging the magnet includes creating a magnetic field pattern with the magnet to produce an arrangement pattern of the micro tissue grafts.

10. The method of claim 1, wherein the magnetic coating includes optically transparent magnetic material.

11. The method of claim 1, wherein the magnetic coating includes particles that are outside a size range of permanent tattoo particles so that any of the particles that become entrapped under the upper surface during harvesting of the plurality of micro tissue grafts or applying the tissue construct are sized to be cleared during natural tissue turnover.

12. The method of claim 1, wherein harvesting the plurality of micro tissue grafts from the donor site includes, for each of the plurality of micro tissue grafts, using a harvesting needle to cut through the donor site along a tissue cutting boundary, and wherein applying the magnetic coating to the donor site includes applying the magnetic coating to an entire surface area of the donor site, including areas outside the tissue cutting boundaries of the plurality of micro tissue grafts.

13. The method of claim 1, wherein harvesting the plurality of micro tissue grafts from the donor site includes, for each of the plurality of micro tissue grafts, using a harvesting needle to cut through the donor site along a tissue cutting boundary, and wherein applying the magnetic coating to the donor site includes applying the magnetic coating to harvest areas of the donor site that are within the tissue cutting boundaries of the plurality of micro tissue grafts.

14. The method of claim 1 and further comprising forming a plurality of tissue constructs and applying the plurality of tissue constructs to the recipient site side-by-side.

15. A method for assembling a plurality of micro tissue grafts, the method comprising:
   applying a magnetic coating over a surface of a donor site;
   harvesting the plurality of micro tissue grafts from the donor site, using one or more harvesting tools configured to extract small tissue columns, so that an upper surface of each of the plurality of micro tissue grafts contains the coating;
   arranging a magnet over the magnetic coating to induce the plurality of micro tissue grafts to organize in a desired orientation;
   forming a solid tissue construct containing the plurality of micro tissue grafts arranged in the desired orientation by one of: inducing a supportive material to solidify around the plurality of micro tissue grafts, allowing the plurality of micro tissue grafts to dry together, or using the magnet to hold the plurality of micro tissue grafts together as a solid construct;
   applying the tissue construct to a recipient site; and
   removing the magnetic coating from the plurality of micro tissue grafts after forming the tissue construct.

16. The method of claim 15, wherein forming the tissue construct includes embedding the plurality of micro tissue grafts, arranged in the desired orientation, in a supportive matrix material.

17. The method of claim 15, wherein the magnetic coating includes iron oxide particles mixed with a material capable of liquefying in response to one of a light, chemical or temperature trigger, and wherein removing the magnetic coating includes triggering the material to liquefy.

18. The method of claim 15, wherein forming the tissue construct includes densely packing the plurality of micro tissue grafts together in contact with one another and allowing the plurality of micro tissue grafts to dry, while in contact with each other, for a time period after harvesting, causing the plurality of micro tissue grafts to stick together.

19. The method of claim 18 and further comprising applying one of an adhesive dressing or tissue adhesive to an upper surface of the tissue construct.

20. A method for assembling a plurality of micro tissue grafts using magnetic assistance, the method comprising:
   replacing needles of a needle harvesting array with coating applicators;
   applying a magnetic coating to harvesting areas of a donor site using the coating applicators;
   replacing the coating applicators within the needle harvesting array with the needles;
   harvesting the plurality of micro tissue grafts from each of the harvesting areas, so that an upper surface of each of the plurality of micro tissue grafts contains the coating;
   arranging a magnet over the magnetic coating to induce the plurality of micro tissue grafts to organize in a desired orientation;
   forming a tissue construct containing the plurality of micro tissue grafts arranged in the desired orientation; and
   applying the tissue construct to a recipient site.

21. The method of claim 20, wherein the coating applicators include diameters one of equal to or smaller than the needles.

22. The method of claim 20, wherein the magnetic coating includes powdered iron oxide mixed with a silicone gel.

23. The method of claim 22, wherein the powdered iron oxide includes particles less than 0.5 micrometers.

* * * * *